(12) United States Patent
Baranov et al.

(10) Patent No.: US 10,772,979 B2
(45) Date of Patent: Sep. 15, 2020

(54) SANITIZING DEVICE AND METHOD FOR SANITIZING ARTICLES

(71) Applicant: LIMESTONE LABS LIMITED, Toronto (CA)

(72) Inventors: Oleg Baranov, Toronto (CA); Graeme Clark, Toronto (CA); Tyler Lypaczewski, Toronto (CA); Taylor Mann, Brantford (CA); Scott Mason, Toronto (CA); Mehrdad Taghizadeh Nouei, Richmond Hill (CA); Geoff Hoy, Toronto (CA); Mohamed Adel Ibrahim, Kingston (CA); Noaman Makki, Ajax (CA)

(73) Assignee: LIMESTONE LABS LIMITED, Toronto (CA)

( * ) Notice: Subject to any disclaimer, the term of this patent is extended or adjusted under 35 U.S.C. 154(b) by 372 days.

(21) Appl. No.: 15/568,927

(22) PCT Filed: Apr. 22, 2016

(86) PCT No.: PCT/IB2016/052309
§ 371 (c)(1),
(2) Date: Oct. 24, 2017

(87) PCT Pub. No.: WO2016/170511
PCT Pub. Date: Oct. 27, 2016

(65) Prior Publication Data
US 2018/0117192 A1    May 3, 2018

Related U.S. Application Data

(60) Provisional application No. 62/152,149, filed on Apr. 24, 2015.

(51) Int. Cl.
*A61L 2/10* (2006.01)
*A61L 2/24* (2006.01)
*A61L 2/08* (2006.01)

(52) U.S. Cl.
CPC ...... *A61L 2/10* (2013.01); *A61L 2/08* (2013.01); *A61L 2/24* (2013.01); *A61L 2202/11* (2013.01);
(Continued)

(58) Field of Classification Search
CPC ..... A61L 2/10; A61L 2/08; A61L 2/24; A61L 2202/14; A61L 2202/122; A61L 2202/121; A61L 2202/11
See application file for complete search history.

(56) References Cited

U.S. PATENT DOCUMENTS 6,190,609 B1 *  2/2001  Chapman ............ A61L 2/0011
                                                422/24
6,458,331 B1   10/2002  Roberts
(Continued)

FOREIGN PATENT DOCUMENTS

CA       2406022 A1    11/2001
WO    2011085127 A1     7/2011

OTHER PUBLICATIONS

International Search Report dated Jun. 23, 2016 issued from the Canadian Intellectual Property Office relating to PCT International Application No. PCT/IB2016/052309.
(Continued)

*Primary Examiner* — Regina M Yoo
(74) *Attorney, Agent, or Firm* — Perry + Currier

(57) ABSTRACT

A sanitizer includes a shell defining first and second chamber portions, and having an opening into the first portion. A cover has a closed position over the opening for preventing access to the chamber, and an open position for permitting
(Continued)

access to the chamber. A tray is moveable between an access position in the first portion, for placement and retrieval of an article within the tray, and a sanitizing position in the second portion, for exposing the article to sanitizing electromagnetic radiation from an emitter mounted in the second portion. A controller controls an actuator coupled to the tray to move the tray to the sanitizing position when the cover is closed, and to return the tray to the access position when a return condition is satisfied. A radiation barrier is configured to substantially prevent radiation from reaching the opening when the tray is in the access position.

19 Claims, 10 Drawing Sheets

(52) U.S. Cl.
CPC ... *A61L 2202/121* (2013.01); *A61L 2202/122* (2013.01); *A61L 2202/14* (2013.01)

(56) References Cited

U.S. PATENT DOCUMENTS

| | | | |
|---|---|---|---|
| 6,461,568 B1 | 10/2002 | Eckhardt | |
| 6,490,351 B1 | 12/2002 | Roberts | |
| 7,128,075 B2* | 10/2006 | Publ | B08B 3/006 |
| | | | 134/107 |
| 7,360,625 B2 | 4/2008 | Stickley | |
| 7,560,706 B1 | 7/2009 | Castelluccio | |
| 7,601,298 B2 | 10/2009 | Humayun et al. | |
| 8,481,970 B2 | 7/2013 | Cooper et al. | |
| 9,339,576 B2 | 5/2016 | LaPorte et al. | |
| 2002/0146343 A1 | 10/2002 | Jenkins et al. | |
| 2003/0150475 A1 | 8/2003 | Abrams et al. | |
| 2004/0147293 A1 | 7/2004 | Park | |
| 2006/0147339 A1 | 7/2006 | Hunter et al. | |
| 2009/0218512 A1 | 9/2009 | Ranta et al. | |
| 2010/0003175 A1 | 1/2010 | Gibson | |
| 2010/0044582 A1 | 2/2010 | Cooper et al. | |
| 2010/0266445 A1 | 10/2010 | Campagna | |
| 2010/0314553 A1 | 12/2010 | Yerby | |
| 2013/0063922 A1 | 3/2013 | La Porte et al. | |
| 2014/0264075 A1 | 9/2014 | LaPorte et al. | |
| 2014/0363335 A1 | 12/2014 | Dam | |
| 2015/0250907 A1 | 9/2015 | Bilenko et al. | |

OTHER PUBLICATIONS

Written Opinion dated Jun. 23, 2016 issued from Canadian Intellectual Property Office relating to PCT International Application No. PCT/IB2016/052309.

ISA/IB International Preliminary Report on Patentability (Chapter I), dated Oct. 24, 2017 re PCT International Patent Application No. PCT/IB2016/052309.

* cited by examiner

SANITIZING DEVICE AND METHOD FOR SANITIZING ARTICLES

CROSS-REFERENCE TO RELATED APPLICATION

This application claims priority from U.S. provisional application No. 62/152,149, filed Apr. 24, 2015, the contents of which is incorporated herein by reference.

FIELD

This invention relates to sanitizing articles such as portable electronic devices. More specifically, the invention comprises a sanitizing device and method to sanitize articles using electromagnetic radiation.

BACKGROUND

The surfaces of portable articles such as smartphones can carry various infectious agents, such as bacteria and viruses. There are many known devices for sanitizing such articles. Most conventional sanitizing devices make use of these ultraviolet bulbs emitting light in the 254 nm wavelength range. For example, the PhoneSoap® is a consumer product used to disinfect smartphones (for example while charging the smartphone overnight). A user places their smartphone inside the single compartment of the PhoneSoap, and an ultraviolet bulb then disinfects the surfaces of the device over a period of time (e.g. 5 minutes).

Conventional sanitizing devices such as those mentioned above may not be suitable for some applications, such as scenarios in which larger numbers of articles are treated in a given time period, because their sanitation cycles impose excessive wear on the ultraviolet bulbs.

SUMMARY

An aspect of the specification provides a sanitizer for sanitizing an article, comprising: a shell defining a first portion and a second portion of a chamber, and having an opening into the first portion of the chamber; a cover having a closed position over the opening for preventing access to the first portion, and an open position for permitting access to the first portion; an emitter of sanitizing electromagnetic radiation mounted in the second portion of the chamber; a tray moveable between (i) an access position in the first portion of the chamber, for placement and retrieval of the article within the tray, and (ii) a sanitizing position in the second portion of the chamber, for exposing the article to the sanitizing electromagnetic radiation; an actuator coupled to the tray for moving the tray between the access position and the sanitizing position; a controller connected to the actuator, and configured to: responsive to detecting that the cover is in the closed position, control the actuator to move the tray to the sanitizing position; and responsive to detecting that a return condition is satisfied, control the actuator to return the tray to the access position; and a radiation barrier, configured to substantially prevent sanitizing electromagnetic radiation from reaching the opening when the tray is in the access position.

BRIEF DESCRIPTIONS OF THE DRAWINGS

Embodiments are described with reference to the following figures, in which.

DETAILED DESCRIPTION OF THE EMBODIMENTS

Figure 1:
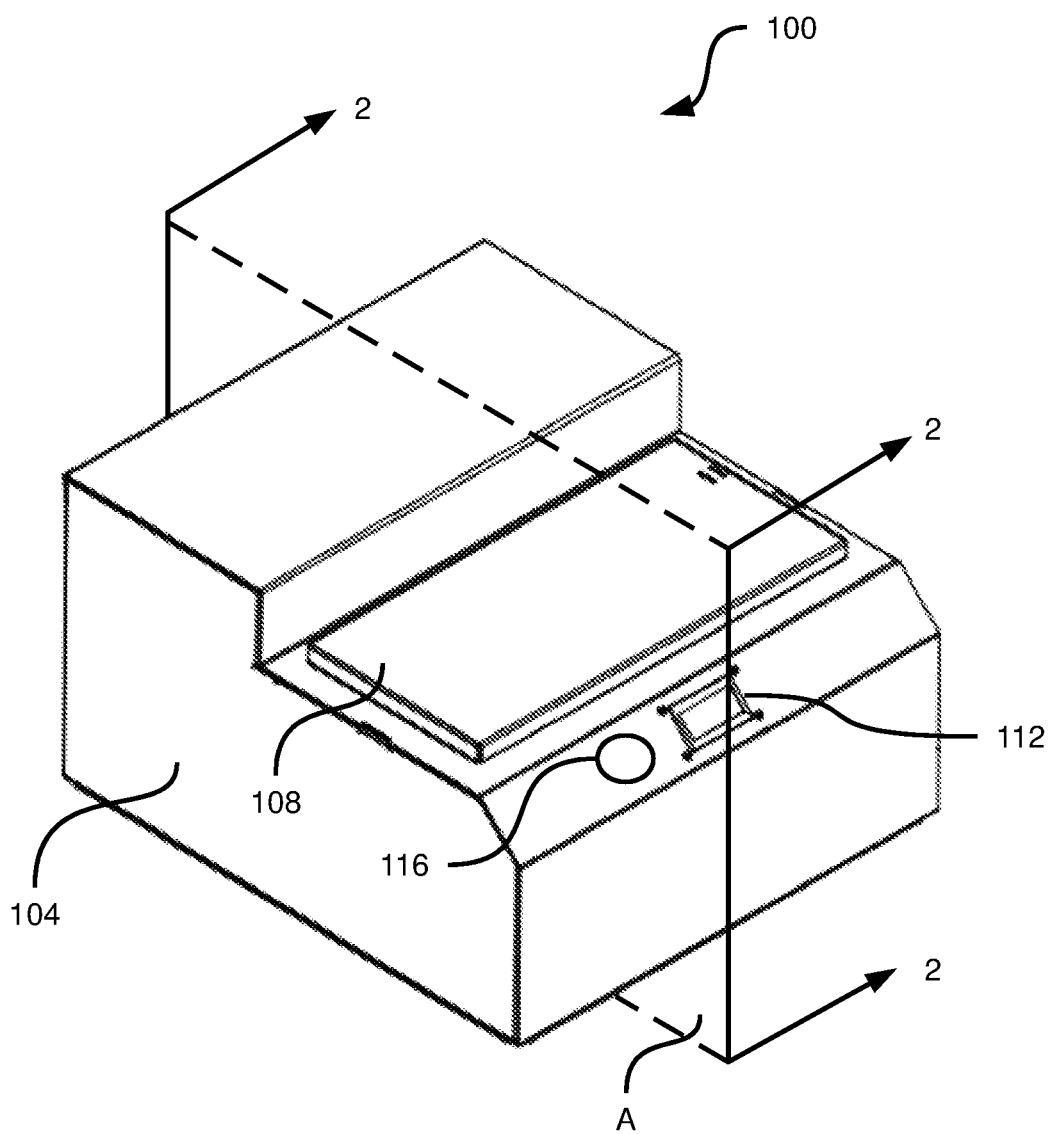
FIG. 1 is an isometric view of a sanitizing device, according to a non-limiting embodiment.

FIG. 1 depicts a sanitizing device 100, also referred to herein simply as a sanitizer 100, for sanitizing articles. As will be apparent from the discussion below, sanitizer 100 is particularly suitable for sanitizing portable articles such as portable electronic devices (PEDs, e.g. smartphones and other mobile phones, pagers, tablet computers and other portable computing devices, wireless headsets, portable media devices, digital cameras, audio and/or video recorders, portable gaming devices, electronic reading devices, navigation devices such as Global Positioning System (GPS) units, and the like), writing implements (e.g. pencils, pens and the like), and so on. As mentioned earlier, such articles tend to attract and harbor potentially harmful organisms or other pathogens, such as bacteria and other microbes, viruses, and the like. Sanitizing such articles is the process of treating the articles to kill or otherwise inactivate the above-mentioned organisms. As will now be apparent, sanitizing may not kill or inactivate every organism present on the article. In some embodiments, sanitizing involves a six-log reduction in the population of at least certain organisms (e.g. Methicillin-resistant *Staphylococcus aureus*). In other embodiments, however, a lesser reduction is permissible.

In general, sanitizer 100 operates to sanitize articles such as PEDs by exposing the PEDs to sanitizing electromagnetic radiation, which may also be referred to as sanitizing electro-optical (EO) radiation. It is noted, however, that the use of the term "electro-optical" does not indicate that the sanitizing electromagnetic radiation is necessarily visible to humans (i.e. falls within the visible spectrum, having a wavelength between about 390 nm and about 700 nm), or indeed any other particular vision system. Sanitizing electromagnetic radiation and sanitizing electro-optical radiation, rather, refer to any suitable wavelength of electromagnetic radiation that is capable of sanitizing a surface. In some embodiments, the sanitizing electromagnetic radiation is ultraviolet radiation. Example wavelength ranges of ultraviolet radiation that can be employed by sanitizer 100 include 100-280 nm (i.e. type C UV); 280-315 nm (i.e. type B UV); 200-300 nm (i.e. middle UV); and 122-200 nm (i.e. far UV). Other wavelength ranges may also be employed, including those that are sufficiently energetic to also be referred to as ionizing radiation (e.g. extreme UV, with a wavelength of 10-120 nm).

In some embodiments, sanitizer 100 can sanitize articles using a single wavelength of radiation. In other embodiments, combinations of different wavelengths may be employed, such as any suitable selection of the wavelengths listed above. In further embodiments, a series of different wavelengths may be applied according to a particular sequence or pattern.

Sanitizer 100 includes a housing, also referred to as a shell, 104. As will be described below in greater detail, shell 104 defines a chamber, or cavity, into which an article may be placed for sanitizing. Sanitizer 100 also includes a cover 108 for opening and closing (i.e. allowing access to and preventing access to) the above-mentioned chamber. Shell 104 can also support a display 112 (e.g. an LCD display), and an interrupt button 116, the operation of which will be described below.

The shape and construction of shell 104 are not particularly limited. In general, shell 104 is shaped to accommodate the internal components of sanitizer 100, to be discussed below. Shell 104 is also opaque to the sanitizing electromagnetic radiation mentioned above. For example, shell 104 can be made of any suitable combination of metals (e.g. steel, aluminum), plastics and the like that absorb or internally reflect (or a combination thereof) the sanitizing electromagnetic radiation.

Figure 2:
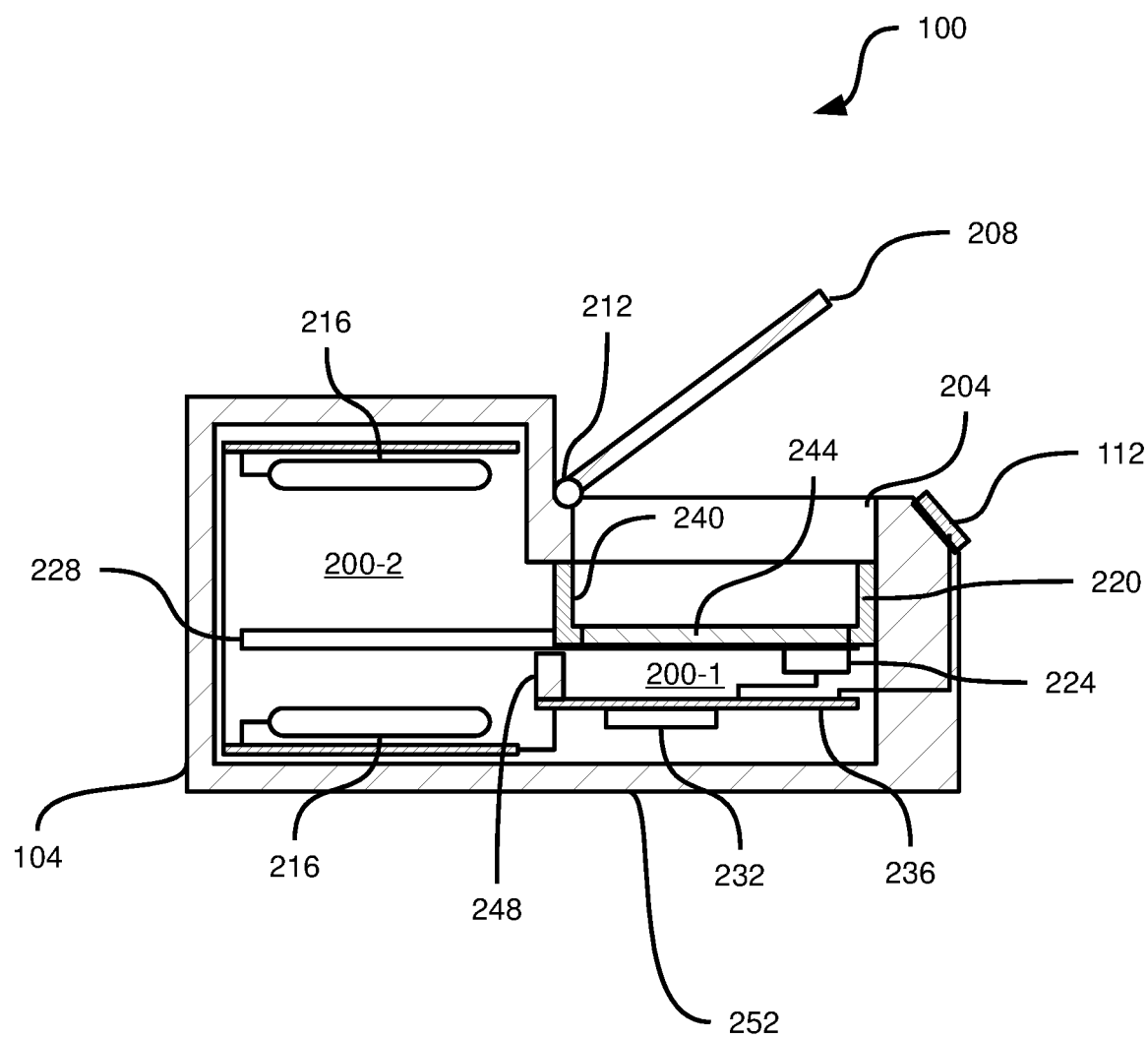
FIG. 2 is a cross-sectional elevation view of the sanitizing device of FIG. 1 with the tray in the access position, taken along the plane labelled 2-2-2 in FIG. 1, according to a non-limiting embodiment.

Referring now to FIG. 2, a cross-sectional view of sanitizer 100 is shown, revealing certain internal components of sanitizer 100. Housing or shell 104 defines an internal chamber, with a first portion 200-1 and a second portion 200-2 (collectively referred to as chamber 200). Shell 104 also includes an opening 204 into first portion 200-1 of the chamber. As will be seen below, opening 204 permits the placement of an article (not shown) into sanitizer 100, and the removal of the article from sanitizer 100. Sanitizer 100 also includes a cover 208. Cover 208 has a closed position over opening 204, for preventing access to first portion 200-1 of the chamber, and an open position for permitting access to first portion 200-1. In FIG. 2, as will now be apparent, cover 208 is shown in the open position.

Cover 208 can take a wide variety of forms. In the present example, cover 208 is rotatably coupled to shell 104, and movable about an axis 212 between the open and closed positions. In other embodiments, cover 208 can be entirely removable from shell 104 (e.g. in the closed position, cover 208 is placed against opening 204, and in the open position, cover 208 is simply removed). In further embodiments, cover 208 can slide between the open and closed positions rather than rotate. Cover 208, in the present example, is a single cover. In other embodiments, however, a plurality of covers can cooperate to permit and prevent access to portion 200-1 of the chamber via opening 204. For instance, cover 208 can be provided by a pair of door-like members that rotate on independent axes to open or close opening 204.

Sanitizer 100 also includes an emitter 216 of sanitizing electromagnetic radiation, mounted in second portion 200-2 of the chamber. In the present embodiment, sanitizer 100 includes a plurality of emitters 216, mounted in upper and lower regions, respectively, of chamber portion 200-2. Emitters 216, in the present example, are ultraviolet bulbs.

Figure 3:
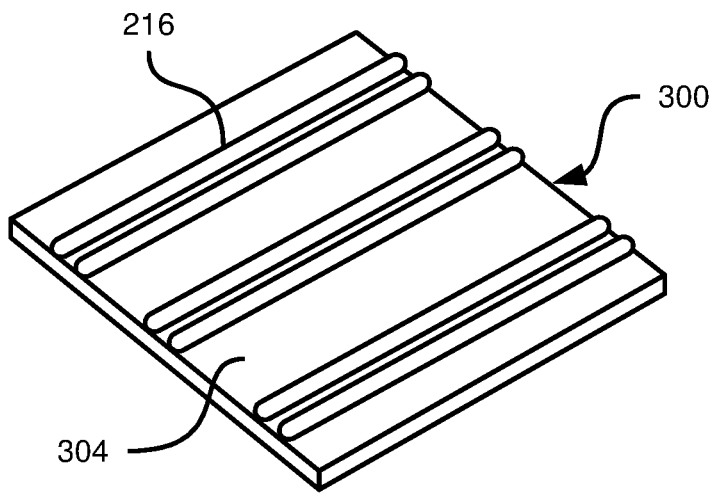
FIG. 3 is an isometric view of an emitter assembly employed in the sanitizing device of FIG. 1, according to a non-limiting embodiment.

Turning to FIG. 3, an example emitter assembly 300 is depicted. Assembly 300 includes a plurality of emitters 216 (in the present example, a total of six emitters 216, arranged in three pairs) supported by a substrate member 304, such as a printed circuit board. Member 304 carries control signals (e.g. from a controller, to be discussed below) to control the energetic output of emitters 216, and also delivers electrical power to emitters 216 from a power source, such as a power supply unit (either within or outside shell 104) connected to a wall outlet, a battery, or the like.

Returning to FIG. 2, it can be seen that two assemblies 300 are employed in the present embodiment, with one disposed in an upper region of chamber portion 200-2, and the other disposed in a lower region of chamber portion 200-2. Each assembly 300—and emitters 216, more generally, when assemblies 300 are not used—is mounted to the internal walls of shell 104 by any suitable means (e.g. mechanical fasteners, adhesives, and the like). It is also contemplated that the inner walls of chamber portion 200-2 are reflective; walls 240 of tray 220 can also be reflective. For example, shell 104 can be fabricated from aluminum, and the interior walls in chamber portion 200-2 can be polished. In other embodiments, the interior walls in chamber portion 200-2 can be treated or overlaid with reflective materials (e.g. paint, plating, and the like).

Sanitizer 100 also includes a tray 220 movable between an access position (illustrated in FIG. 2) in first chamber portion 200-1, for placement and retrieval of an article within tray 220, and a sanitizing position in second chamber portion 200-2, for exposing the article to sanitizing electromagnetic radiation emitted by emitters 216.

Tray 220 is movable between the above-mentioned positions by the operation of an actuator 224 coupled to tray 220. In the present embodiment, actuator 224 is a motor (e.g. an electric stepper motor) mounted within shell 104 and connected to tray 220 for driving tray 220 along rails 228 disposed on either side of tray 220. Various arrangements are contemplated for actuator 224. For example, the above-mentioned electric motor can be mounted on tray 220 itself, and include a gear or wheel that engages with a rail 228 to move tray 220 along rails 228. Various other actuators may also be employed, including pneumatic or hydraulic actuators, a belt drive or the like.

Sanitizer 100 also includes a controller 232, in the form of one or more integrated circuits mounted on a control board 236. The components of controller 232 will be described in greater detail below. In general, controller 232 is connected to actuator 224, as well as emitters 216 (for example, via substrate members 304) and various other components of sanitizer 100, and is configured to place sanitizer in various operating states. More specifically, controller 232 is configured, responsive to detecting that cover 208 is in the closed position, to control actuator 224 to move tray 220 from the access position shown in FIG. 2 to the sanitizing position (to be illustrated later). Controller 232 is also configured, responsive to detecting that a return condition is satisfied, to control actuator 224 to return tray 220 from the sanitizing position to the access position (e.g. to allow removal of a now-sanitized article from tray 220).

Sanitizer 100 also includes a radiation barrier, which in the present embodiment is connected to tray 220, configured to substantially prevent sanitizing electromagnetic radiation from reaching opening 204 when tray 220 is in the access position. As is apparent from FIG. 2, when tray 220 is in the access position, cover 208 may be opened to place an article in tray 220 or retrieve an article from tray 220. Thus, if emitters 216 are powered on, radiation from emitters 216 may undesirably escape shell 104 via opening 204 in the absence of any barriers to such escape. Tray 220 therefore includes at least one wall 240 that is substantially opaque to the sanitizing electromagnetic radiation and, in the access position, substantially abuts with the interior wall of shell 104 to prevent sanitizing electromagnetic radiation from emitters 216 from escaping via opening 204.

Figure 4:
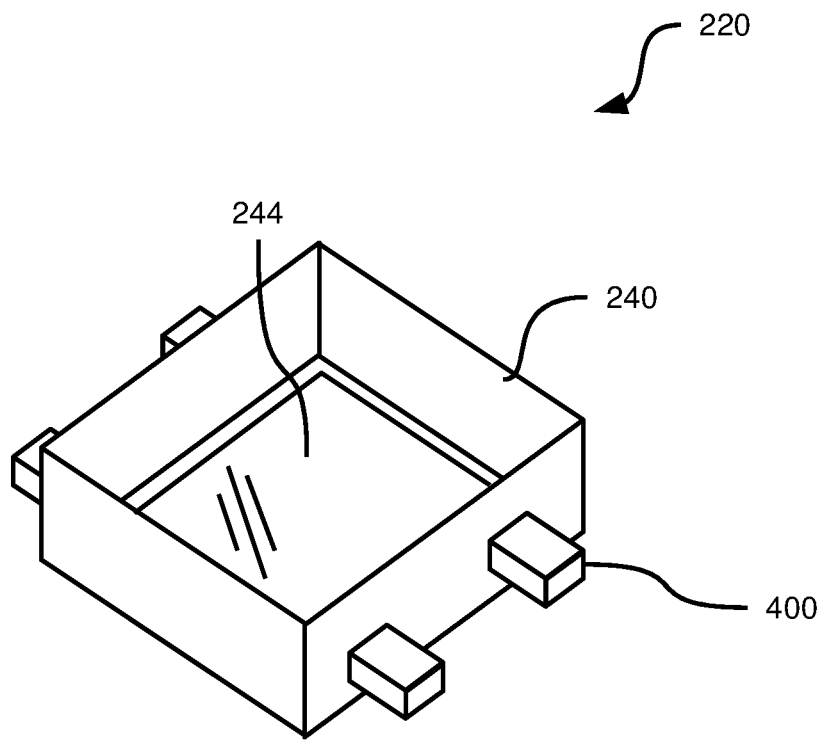
FIG. 4 is an isometric view of a tray employed in the sanitizing device of FIG. 1, according to a non-limiting embodiment.

In addition, tray 220 includes, in the present example, a radiation-transparent (or at least translucent) lower portion 244, that allows radiation from the lower emitters 216 to reach the article on tray 220 in the sanitizing position. Referring briefly to FIG. 4, tray 220 is shown in isolation, illustrating walls 240 and lower portion 244 (which, as will now be apparent, carries the article to be sanitized). Tray 220 also includes, in the present embodiment, a plurality of brackets 400—for example, a pair of brackets on each of two opposite walls 240—extending outwardly from walls 240 for supporting tray 220 on rails 228.

Although lower portion 244 is illustrated as being a solid transparent or translucent wall (e.g. made of fused quartz, clear plastic or the like), in other embodiments a variety of other structures may be employed for lower portion 244. For example, lower portion 244 may be a mesh or cage made of any suitable metal or plastic, the spaces between mesh elements being transmissive to the sanitizing electromagnetic radiation.

Returning to FIG. 2, sanitizer 100 can include an additional barrier 248 (e.g. formed as an interior part of shell 104) that acts, along with control board 236, to reduce or eliminate the leakage of radiation from emitters 216 to opening 204.

The components of sanitizer 100 need not be arranged within and on shell 104 exactly as shown in FIG. 2. For example, control board 236 and screen 112, in particular, can be placed in a variety of other locations than those shown. As a further example, emitters 216 may be mounted on the inner sides of shell 104, rather than on the "floor" and "ceiling" of chamber portion 200-2, as shown in FIG. 2. Certain advantages may be provided by mounting, for example, control board 236 in the orientation shown in FIG. 2. In particular, a lower wall 252 of shell 104 may be removable to permit maintenance of the internal components of sanitizer 100. The placement of control board 236 as shown in FIG. 2, in combination with the downwards orientation of controller 232 (and, optionally, of one or more of the connectors between control board 236 and other components of sanitizer 100), permits maintenance access to control board 236 and controller 232 simply by removing lower wall 252. That is, disassembly of other parts of sanitizer 100 may be avoided to perform maintenance on control board 236.

Figure 5:
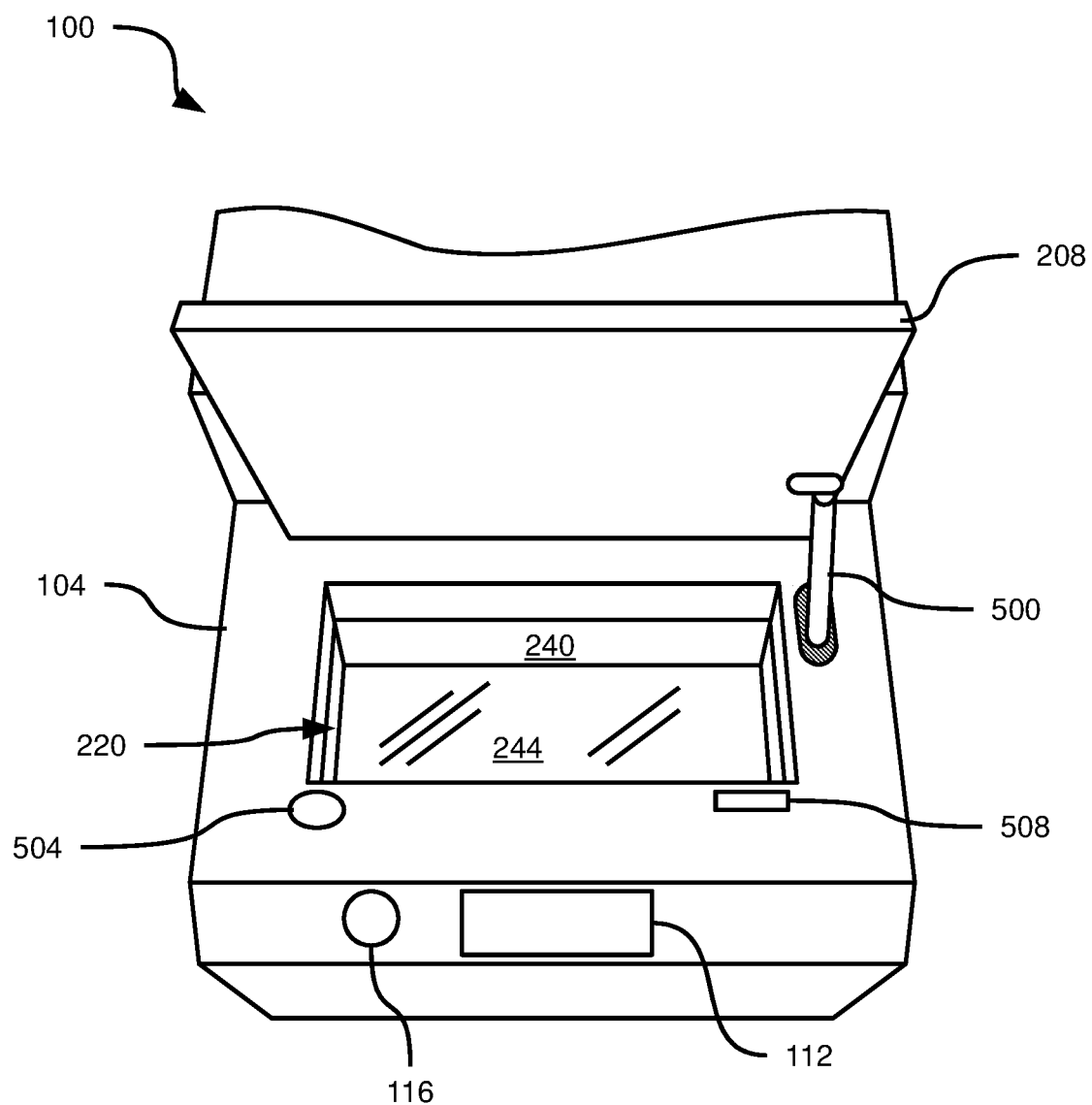
FIG. 5 is a partial front perspective view of the sanitizing device of FIG. 1, according to a non-limiting embodiment.

Referring now to FIG. 5, a partial perspective view of sanitizer 100 is provided from the front of sanitizer 100, with cover 208 in the open position and tray 220 in the access position. As seen in FIG. 5, shell 104 and walls 240 of tray 220 are substantially flush with one another, thus preventing sanitizing electromagnetic radiation from escaping via opening 204. As noted earlier, an addition barrier such as barrier 248 may reduce or eliminate (in cooperation with control board 236, in the present embodiment) radiation leakage through the transparent or translucent lower portion 244 of tray 220.

Also shown in FIG. 5 is a cover actuator 500 connecting cover 208 and shell 104. In the present example, cover actuator 500 is an electrically-powered linear actuator, although various other actuators are also contemplated, including hydraulic and pneumatic actuators. Cover actuator 500 is connected to controller 232 and thereby controllable to raise and lower cover 208 to permit and prevent access to tray 220. In other embodiments, cover actuator 500 may be omitted, or supplemented with one or more additional cover actuators (not shown). In further embodiments, cover actuator 500 need not be powered or controlled by controller 232, but can instead be a mechanical damper for limiting the speed with which cover 208 is opened or closed (e.g. by an operator of sanitizer 100). In some embodiments, actuator 500 can bias cover 208 towards the open position (e.g. by way of a spring mechanism).

Sanitizer 100 can also include, as illustrated in FIG. 5, a cover sensor 504 such as a mechanical switch, magnetic sensor, light sensor or the like that is configured to detect whether or not cover 208 is in the closed position. Cover sensor 504 is connected to controller 232, which can also be configured, based on the input received from cover sensor 504, to control other aspects of the operation of sanitizer 100. In some embodiments, controller 232 can also be connected to a lock 508, and can control lock 508 to retain cover 208 in the closed position or release cover 208 for transitioning to the open position. The nature of lock 508 is not particularly limited—for example, lock 508 can be electromagnetic, a mechanical switch that engages a corresponding structure on cover 208, and the like.

Figure 6:
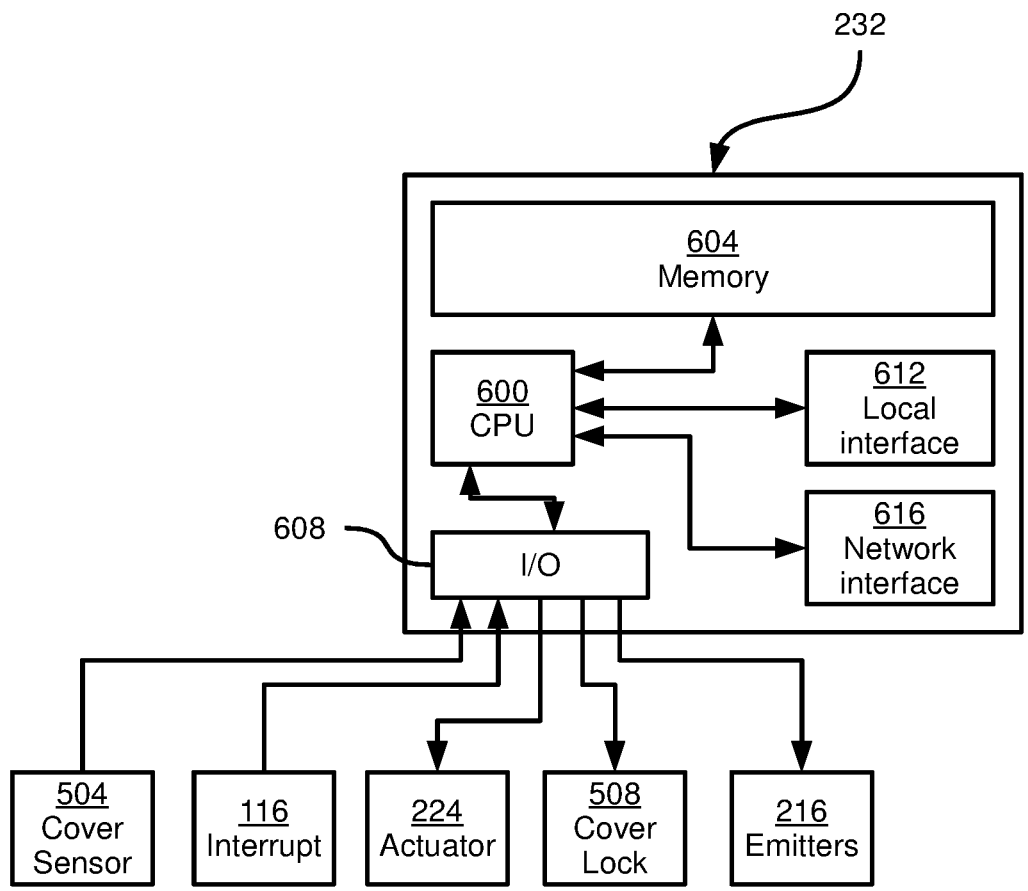
FIG. 6 is a block diagram illustrating certain internal components of a controller of the sanitizing device of FIG. 1, according to a non-limiting embodiment.

Referring now to FIG. 6, controller 232 is shown in greater detail. In particular, controller 232 includes a central processing unit (CPU), also referred to as a processor 600, coupled to a non-transitory storage medium in the form of a memory 604. Memory 604 stores computer readable instructions executable by processor 600 to cause processor 600. Processor 200 and memory 204 are generally comprised of one or more integrated circuits (ICs), and can have a variety of structures, as will now occur to those skilled in the art. Processor 600 executes the instructions stored in memory 604 to perform various actions to control the operation of sanitizer 100, as will be discussed below.

Controller 232 also includes an input/output (I/O) interface 608 interconnecting processor 600 with, for example, cover sensor 504, interrupt button 116, actuator 224, cover lock 508 and emitter 216. Controller 232 can also include a local network interface 612, such as an RFID transceiver, an NFC transceiver, a Bluetooth radio assembly, or the like. In addition, controller 232 can include a network interface 616, such as a WiFi radio assembly, an Ethernet controller, and the like (including any suitable combination of the above). In some embodiments, either or both of interfaces 612 and 616 can be omitted. In further embodiments, other communications interfaces can be included, such as a PLC interface for connection to a programmable logic controller (PLC).

Figure 7:
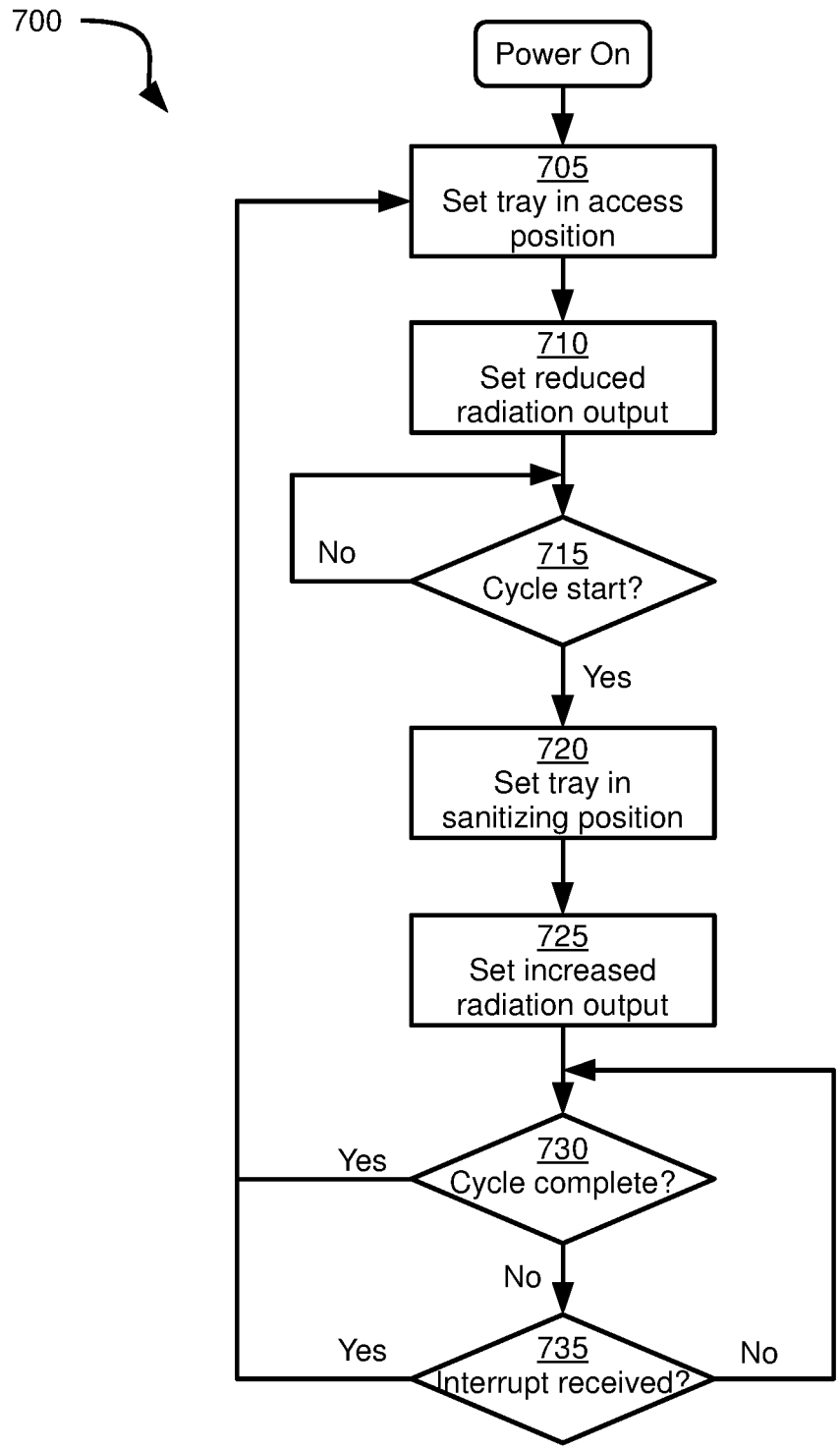
FIG. 7 depicts a method of operating the sanitizing device of FIG. 1, according to a non-limiting embodiment.

Turning now to FIG. 7, the operation of sanitizer 100 will be discussed in greater detail. More specifically, FIG. 7 illustrates a method 700 of operating sanitizer 100. The blocks of method 700 are performed by controller 232, and more particularly by processor 600 in cooperation with the other components of controller 232.

At block 705, when sanitizer 100 is supplied with power (or following the completion of a previous sanitizing cycle, as will be discussed below), controller 232 is configured to set tray 220 in the access position. For example, the performance of block 705 can include sending a predefined position to actuator 224 (which, as noted earlier, may be a stepper motor and can therefore be responsive to positional commands) that causes actuator 224 to move tray 220 to the access position shown in FIG. 2, if tray 220 is not already in the access position. In some embodiments, controller 232 can simply send the above-mentioned position or other instruction to actuator 224 regardless of the current position of tray 220. In other embodiments, controller 232 can be configured to instruct actuator 224 to move tray 220 only if tray 220 is not already in the access position (as indicated, for example, by a tray position sensor connected to controller 232).

Also at block 705, if lock 508 is implemented, controller 232 can disengage lock 508 responsive to receiving confirmation that tray 220 is in the access position. Such confirmation can be received in the form of a signal from actuator 224 or the above-mentioned tray position sensor. In other embodiments, the above-mentioned confirmation step can be omitted, and controller 232 can instead be configured to disengage lock 508 (for example, by cutting power to an electromagnet) a predefined time period (e.g. stored in memory 604) after instructing actuator 224 to move tray 220 to the access position. As will now be apparent, at block 705 lock 508 is not necessarily engaged. For example, if sanitizer 100 has just been powered on, lock 508 may begin in a disengaged state. In such embodiments, controller 232 may still send an instruction to disengage lock 508; alternatively, controller 232 can be configured to determine (e.g. by an input signal received from lock 508 indicating its current state) whether lock 508 is currently engaged or disengaged.

At block 710, controller 232 is configured to control emitters 216 to set a reduced radiation output by emitters 216. The reduced radiation output can be zero (that is, at block 710 emitters 216 can be turned off, or remain off if sanitizer 100 has just been powered on). Preferably, however, controller 232 is configured to select maintain at least two power levels for emitters 216. A first one of the power levels, also referred to as a standby power level, is selected when tray 220 is in the access position, while a second power level, also referred to as a treatment power level, is selected when tray 220 is in the sanitizing position. The first power level is lower than the second power level. That is, at the first power level, emitters 216 emit a lower amount of radiation per unit time, and thus generally also consume less electrical energy.

Although block 710 is illustrated as following block 705, in some embodiments, block 710 can be performed before, or simultaneously with, block 705. In some embodiments, block 710 can be omitted and emitters 216 can instead operate at full power (that is, at the second power level mentioned above) at all times.

At block 715, controller 232 is configured to determine whether to begin a sanitization cycle. In the present embodiment, in which sanitizer 100 includes cover sensor 504, the determination at block 715 is a determination of whether an input signal has been received from cover sensor 504 indicating that cover 208 is in the closed position. In such embodiments, cover 208 is preferably biased towards the open position, such that upon unlocking of cover 208 at block 705, cover 208 does not remain in the closed position if it was previously closed.

In other embodiments, the determination at block 715 can take various other forms. For example, sanitizer 100 can include an additional input switch or button for depression by an operator of sanitizer 100 after an article 100 has been placed in tray 220 and cover 208 has been closed. The determination at block 715, in such embodiments, is a determination as to whether the additional input has been depressed or otherwise activated. Preferably, such embodiments also include cover sensor 504, and the determination at block 715 is a determination of whether the additional input has been activated and cover 208 is closed.

When the determination at block 715 is negative, performance of method 700 remains at block 715 (that is, the determination is repeated). When the determination at block 715 is affirmative, however, performance of method 700 proceeds to block 720.

At block 720, controller 232 is configured to set tray 220 in the sanitizing position. More specifically, controller 232 is configured to instruct actuator 224 to move to a predefined position, to cause actuator 224 to move tray 220 to the sanitizing position. In embodiments in which lock 508 is present, at block 720 controller 232 can also be configured to engage lock 508 prior to setting tray 220 to the sanitizing position.

Figure 8:
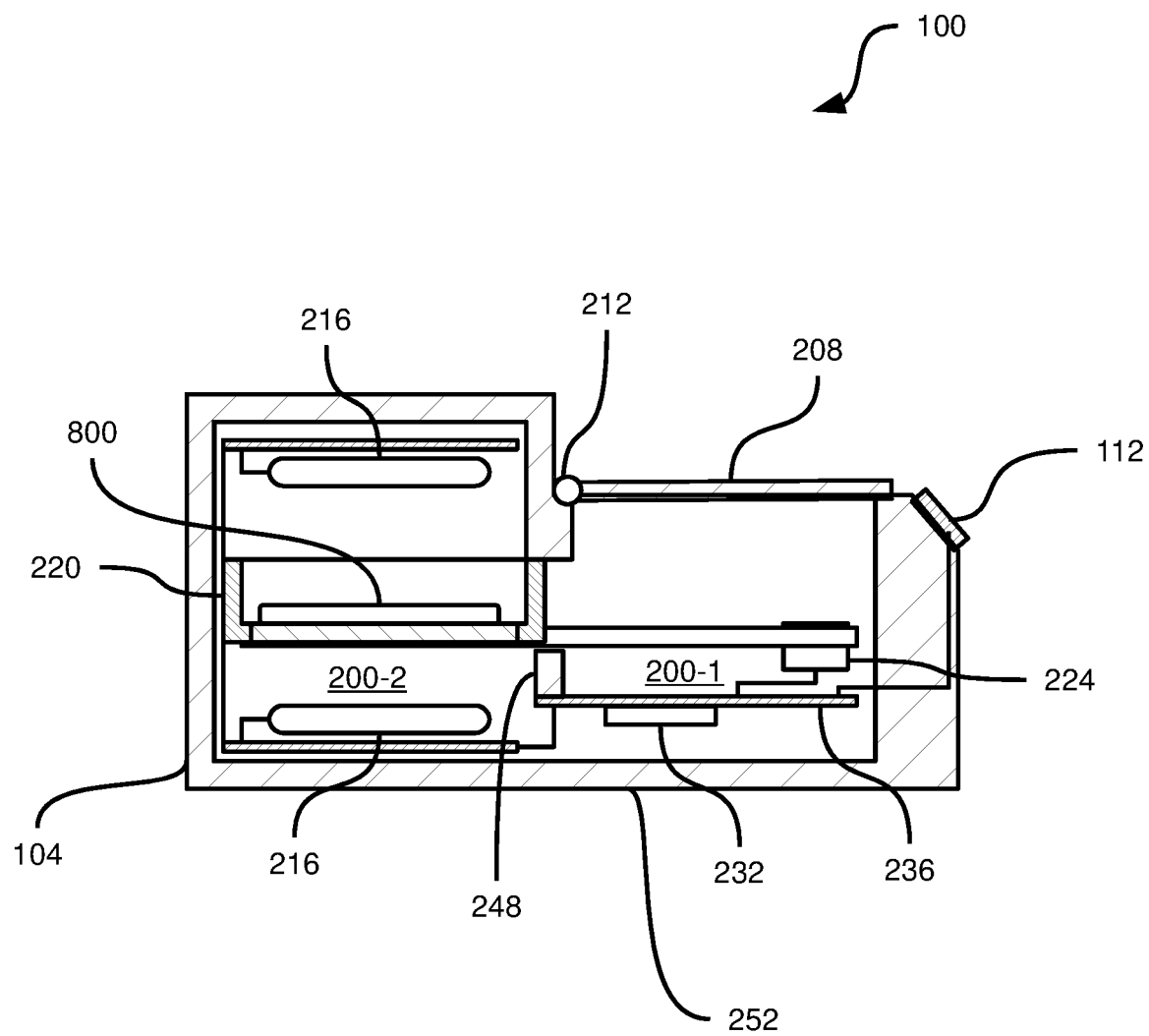
FIG. 8 is a cross-sectional elevation view of the sanitizing device of FIG. 1 with the tray in the sanitizing position, taken along the plane labelled 2-2-2 in FIG. 1 according to a non-limiting embodiment.

Referring briefly to FIG. 8, sanitizer 100 is shown in cross-section (along the same plane as shown in FIG. 2). In FIG. 8, cover 208 is in the closed position and tray 220 has been set in the sanitizing position, in the second chamber portion 200-2. As a result, an article 800 (e.g. a smartphone) contained within tray 220 is exposed to the sanitizing electromagnetic radiation emitted by emitters 216.

Returning to FIG. 7, at block 725 controller 232 is configured to increase the radiation output of emitters 216 to the above-mentioned second power level. If block 710 is omitted, however, block 725 is also omitted. The specific power level selected by controller 232 at block 725 is not particularly limited. For example, a plurality of sanitization power levels can be stored in memory 604, and can be selected either via an input (not shown) manipulated by an operator of sanitizer 100, or automatically by controller 232 based on data received from sensors within chamber portions 200-1 and 200-2 reflecting the size or nature of the article to be sanitized.

As noted above in connection with blocks 705 and 710, the order of blocks 720 and 725 can also be reversed from that shown in FIG. 7. In some embodiments, blocks 720 and 725 can also be performed simultaneously.

At block 730, controller 232 is configured to determine whether the sanitization cycle is complete. A sanitization cycle is referred to as a period of time during which tray 220 (and any article or articles it carries) are in the sanitizing position, exposed to the sanitizing electromagnetic radiation from emitters 216. Controller 232 can be configured, therefore, to start a timer following the performance of block 725 (or 720, if block 725 is omitted), and at block 730 to compare the current timer value to a predefined time period stored in memory 604. The time period is not particularly limited. In the present embodiment, cycle time periods between about thirty and about forty-five seconds are contemplated. In other embodiments, however, cycle time periods of less than thirty seconds and of more than forty-five seconds may also be employed. The selected cycle length depends, in part, on the type of sanitizing electromagnetic radiation produced by emitters 216. The above-mentioned range of about thirty to about forty-five seconds, for example, may be an effective cycle length when emitters 216 produce UV-C radiation.

Controller 232 can also be configured to select from a plurality of predefined cycle lengths, or to dynamically determine a length for each cycle, based on a variety of inputs. Those inputs can include any one of, or any suitable combination of, an operator input such as a dial on the exterior of shell 104; the type of radiation produced by emitters 216 (which may be stored in memory 604 or detected via sensors such as quartz photodiodes in chamber portion 200-2); the power output of emitters 216 (which may also be stored in memory 604 or detected via sensors in chamber portion 200-2).

In embodiments in which sanitizer is equipped with local communications interface 612, certain articles—such as portable computing devices equipped with corresponding local communications interfaces—can be detected by controller 232. Controller 232 can be configured to store, in memory 604, records identifying each article so detected, along with times and dates indicating each sanitization cycle that has been performed for the article. Controller 232 can therefore also select a cycle length, power level for emitters 216, or both, based on such records. For example, controller 232 can select a cycle length that is proportional to the amount of time that has passed since the last cycle recorded in memory 604 for the relevant article.

When the determination at block 730 is negative (that is, the cycle is not complete), controller 232 proceeds to block 735. At block 735, controller 232 determines whether an interrupt command has been received. In the present example, in which sanitizer 100 includes interrupt button 116, the determination at block 735 includes a determination of whether button 116 has been activated. Other interrupt signals are also contemplated, such as signals received at controller 232 that are indicative of a failure or other malfunction of emitters 216, actuator 224 or the like.

When the determination at block 735 is negative, controller 232 returns to block 730 and continues to monitor for cycle completion and interrupts. When the determination at either of blocks 730 and 735 is affirmative, however, performance of method 700 returns to block 705, thus ending the current sanitization cycle and preparing sanitizer 100 for the next cycle.

In embodiments in which sanitizer 100 is equipped with screen 112, controller 232 can be configured to control screen 112 to present various information at any one or more of the blocks of method 700. For example, controller 232 can present on screen 112 a current status of sanitizer 100 (e.g. "idle" at block 705, "cycle starting" at block 720, and the like). During the repeated performances of blocks 730 and 735, for example, controller 232 can present a remaining cycle time on screen 112.

Controller 232 can also be configured to transmit data in stored in memory 604 to a server or other computing device (not shown) via network interface 616. Such data can be transmitted at varying frequencies, such as after each completed cycle, or in a batch one or more times per day. The contents of such transmissions can include the above-mentioned records identifying articles detected within tray 220, and can thus include electronic device identifiers, cycle timestamps, durations and the like.

Variations to the structure and operation of sanitizer 100 are contemplated, in addition to those discussed above. For example, in some embodiments, tray 220 can be fixed within shell 104 and emitters 216 can be moved between two positions by one or more actuators. For example, tray 220 can be fixed within first chamber portion 200-1, while emitters 216 can be movable between an idle position in second chamber portion 200-2 and a sanitizing position in first chamber portion 200-1. As will now be apparent, the shape of shell 104 would require modification in such an embodiment, to allow the upper bank of emitters 216 to travel into first chamber portion 200-1 between cover 208 and tray 220.

In further variations, shell 104 can include supporting structures thereon, such as a cage or shelf, for example for holding a container of hand sanitizer. In still further embodiments, the shape of shell 104 and cover 108 can be varied. For example, referring to FIGS. 9 and 10, a sanitizing device 900 is shown, in which many of the components described above are included. Device 900 also includes a shell 904 and cover 908 that are shaped to provide a larger opening than opening 204 provided by shell 104 and cover 108 of device 100. In particular, shell 104 is partially open at the front thereof in addition to the top opening discussed earlier, and cover 108 is shaped to close both the top and front open portions of shell 904 when in the closed position.

Figure 9:
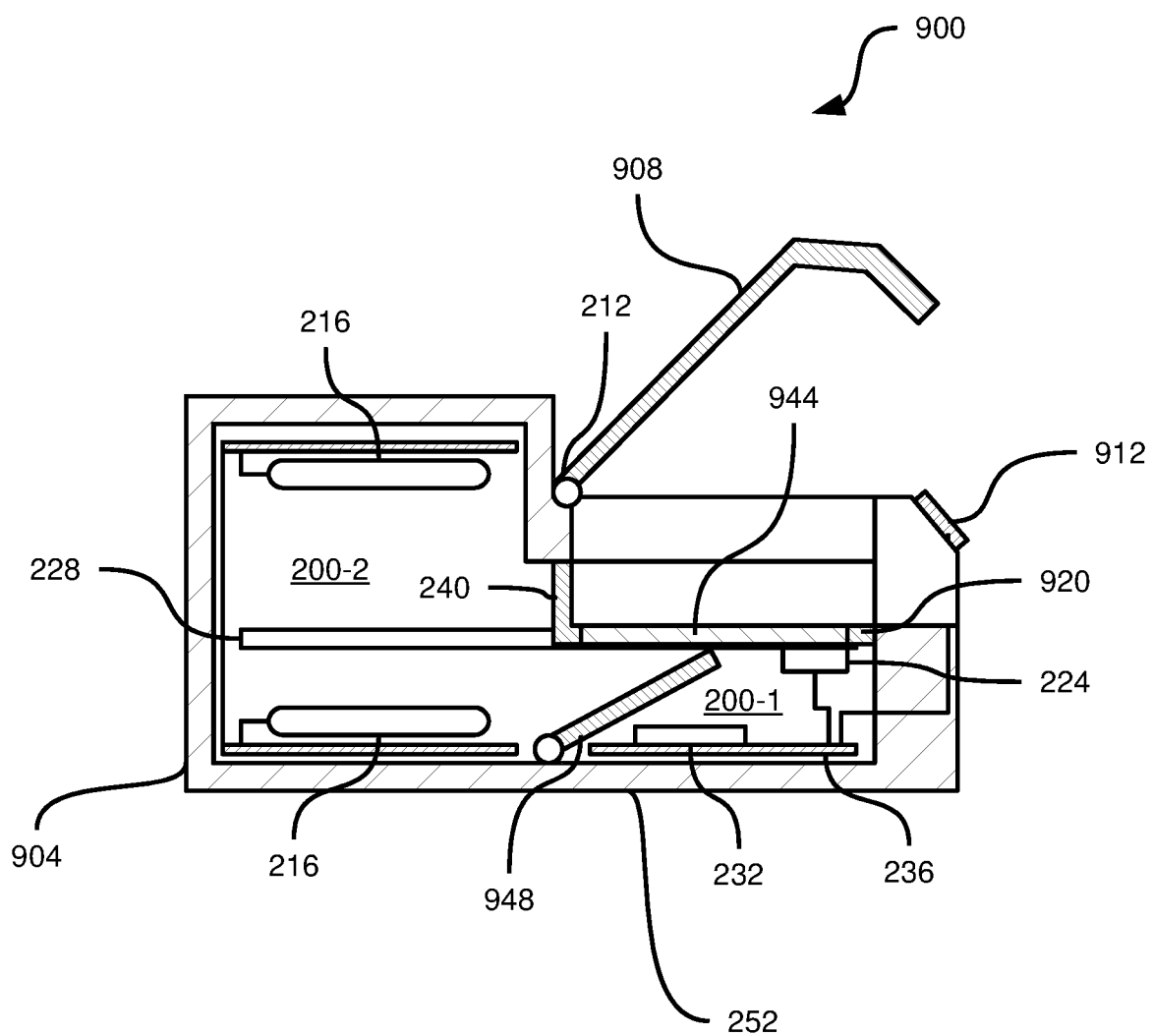
FIG. 9 is a cross-sectional elevation view of a sanitizing device with the tray in the access position, according to another non-limiting embodiment.
Figure 10:
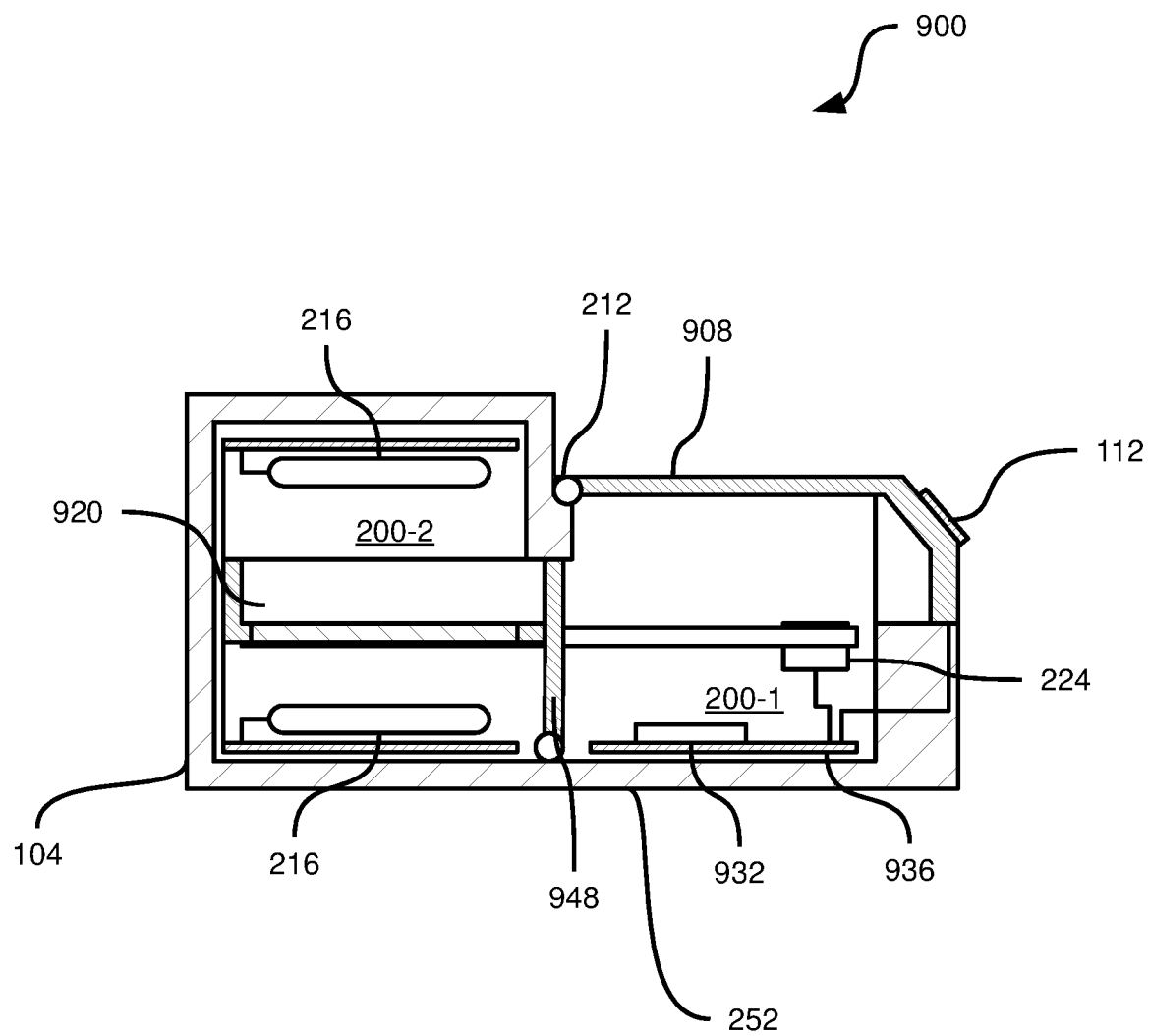
FIG. 10 is a cross-sectional elevation view of the sanitizing device of FIG. 9 with the tray in the sanitizing position, according to another non-limiting embodiment.

FIG. 9 illustrates device 900 with cover 908 in the open position and a tray 920 in the access position, in which a device (e.g. a smartphone, pager or the like) can be placed in tray 920 from a greater variety of directions that in device 100. FIG. 10 illustrates device 900 with cover 908 in the closed position, and tray 920 in the sanitizing position. As will now be apparent, tray 920 also differs structurally from tray 220. In particular, tray 920 does not include a front wall. Device 900 therefore includes an additional barrier 948 rotatably coupled to the interior of shell 904. Barrier 948 is biased towards a raised position, shown in FIG. 10, in order to reduce or eliminate radiation leakage when tray 920 is in the sanitzation position. When tray 920 is moved towards the access position, tray 920 impacts barrier 948 and rotates barrier 948 to a lowered position (shown in FIG. 9).

Further, although electromagnetic radiation is discussed above for sanitizing articles, in other embodiments other forms of sanitizing radiation may be employed.

Certain advantages to the above devices and methods will now be apparent to those skilled in the art. For example, the provision of two chamber portions as discussed above, coupled with a tray (or, as noted earlier, emitters) that is movable between the two chamber portions permits emitters 216 to remain powered on at all times—which may increase the lifespan of emitters 216—while reducing or preventing radiation from exiting sanitizer 100 via opening 204.

Those skilled in the art will appreciate that in some embodiments, the functionality of controller 232 may be implemented using any combination of pre-programmed hardware or firmware elements (e.g., application specific integrated circuits (ASICs), electrically erasable programmable read-only memories (EEPROMs), etc.), or other related components.

The scope of the claims should not be limited by the embodiments set forth in the above examples, but should be given the broadest interpretation consistent with the description as a whole.

The invention claimed is:

1. A sanitizer for sanitizing an article, comprising:
   a shell defining a first portion and a second portion of a chamber, and having an opening into the first portion of the chamber;
   a cover having a closed position over the opening for preventing access to the first portion, and an open position for permitting access to the first portion;
   an emitter of sanitizing electromagnetic radiation mounted in the second portion of the chamber;
   a tray moveable between (i) an access position in the first portion of the chamber, for placement and retrieval of the article within the tray, and (ii) a sanitizing position in the second portion of the chamber, for exposing the article to the sanitizing electromagnetic radiation;
   an actuator coupled to the tray for moving the tray between the access position and the sanitizing position;
   a controller connected to the actuator, and configured to:

responsive to detecting that the cover is in the closed position, control the actuator to move the tray to the sanitizing position; and
responsive to determining that a sanitization cycle is complete, control the actuator to return the tray to the access position; and
a radiation barrier, configured to substantially prevent sanitizing electromagnetic radiation from reaching the opening when the tray is in the access position.

2. The sanitizer of claim 1, further comprising a coupling movably connecting the cover to the shell.

3. The sanitizer of claim 2, wherein the coupling includes a hinge.

4. The sanitizer of claim 1, further comprising a cover actuator connected between the cover and the shell.

5. The sanitizer of claim 4, the cover actuator configured to bias the cover to the open position.

6. The sanitizer of claim 1, further comprising a cover lock switchable between an engaged state to retain the cover in the closed position, and a disengaged state to permit the cover to move to the open position.

7. The sanitizer of claim 6, the cover lock comprising an electromagnet electrically connected to the controller; the controller further configured:
responsive to detecting that the cover is in the closed position, to switch the cover lock to the engaged state; and
responsive to controlling the actuator to return the tray to the access position, to switch the cover lock to the disengaged state.

8. The sanitizer of claim 1, the tray comprising a lower portion for supporting the article; wherein the radiation barrier includes at least one upstanding wall connected to the lower portion.

9. The sanitizer of claim 8, the lower portion comprising a material substantially transparent to the sanitizing electromagnetic radiation.

10. The sanitizer of claim 9, the material including at least one of a mesh and a quartz-based glass.

11. The sanitizer of claim 1, further comprising a cover sensor connected to the controller, the controller configured to determine that the cover is in the closed position by receiving a signal from the cover sensor.

12. The sanitizer of claim 1, further comprising a plurality of emitters.

13. The sanitizer of claim 12, further comprising an emitter assembly including a substrate member supporting the plurality of emitters.

14. The sanitizer of claim 1, the controller further configured to determine that the sanitization cycle is complete by detecting that a predefined time period has elapsed since controlling the actuator to move the tray to the sanitizing position.

15. The sanitizer of claim 1, further comprising an interrupt button; the controller further configured, responsive to detecting an activation of the interrupt button prior to determining that the sanitization cycle is complete, to control the actuator to return the tray to the access position.

16. A method in a sanitizer having (i) a chamber with first and second chamber portions; (ii) a cover having open and closed positions for permitting and preventing access to an opening into the first chamber portion; (iii) an emitter of sanitizing electromagnetic radiation mounted in the second chamber portion; and (iv) a tray moveable between an access position in the first chamber portion, for placement and retrieval of an article within the tray, and a sanitizing position in the second chamber portion, for exposing the article to the sanitizing electromagnetic radiation; the method comprising, at a controller of the sanitizer:
responsive to detecting that the cover is in the closed position, moving the tray to the sanitizing position;
responsive to determining that a sanitization cycle is complete, returning the tray to the access position.

17. The method of claim 16, further comprising:
increasing a radiation output level of the emitter responsive to moving the tray to the sanitizing position.

18. The method of claim 16, further comprising:
decreasing a radiation output level of the emitter, without disabling the emitter, responsive to determining that the sanitization cycle is complete.

19. The method of claim 16, further comprising:
responsive to detecting that the cover is in the closed position, switching a cover lock of the sanitizer to an engaged state to retain the cover in the closed position; and
responsive to returning the tray to the access position, switching the cover lock to a disengaged state to permit the cover to move to the open position.

* * * * *